(12) United States Patent
Azuma et al.

(10) Patent No.: US 9,176,156 B2
(45) Date of Patent: Nov. 3, 2015

(54) AUTOMATIC ANALYZER INCLUDING PRESSURE SENSOR FOR WASHING SOLUTION

(75) Inventors: Shinji Azuma, Hitachinaka (JP);
Masaharu Nishida, Hitachinaka (JP);
Tatsuya Fukugaki, Hitachinaka (JP);
Hirofumi Sasaki, Hitachinaka (JP);
Atsushi Suzuki, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 996 days.

(21) Appl. No.: 13/059,309

(22) PCT Filed: Jul. 31, 2009

(86) PCT No.: PCT/JP2009/063980
§ 371 (c)(1),
(2), (4) Date: Mar. 22, 2011

(87) PCT Pub. No.: WO2010/038546
PCT Pub. Date: Apr. 8, 2010

(65) Prior Publication Data
US 2011/0174343 A1 Jul. 21, 2011

(30) Foreign Application Priority Data
Sep. 30, 2008 (JP) ................................. 2008-252141

(51) Int. Cl.
*G01N 35/10* (2006.01)

(52) U.S. Cl.
CPC .... *G01N 35/1016* (2013.01); *G01N 2035/1018* (2013.01)

(58) Field of Classification Search
CPC ............. G01N 1/00; G01N 1/10; G01N 1/14; G01N 29/4418; G01N 29/449; G01N 35/02; G01N 35/00584; G01N 35/00594; G01N 35/613; G01N 35/623; G01N 35/693; G01N 35/0099; G01N 35/1004; G01N 35/10; G01F 1/00; G01F 7/00
USPC ........... 702/19, 31, 45, 47, 50, 55, 64, 71, 81, 702/82, 98, 100, 138; 422/63; 73/152.18, 73/708; 356/436; 134/113
See application file for complete search history.

(56) References Cited

U.S. PATENT DOCUMENTS

| | | |
|---|---|---|
| 2004/0034479 A1 | 2/2004 | Shimase et al. |
| 2005/0024644 A1 | 2/2005 | Mototsu et al. |
| 2008/0056942 A1 | 3/2008 | Arima et al. |

FOREIGN PATENT DOCUMENTS

| | | |
|---|---|---|
| JP | 11-271323 A | 10/1999 |
| JP | 2000046846 A * | 2/2000 |

(Continued)

OTHER PUBLICATIONS

English Machine Translation of Description of JP 2006189259 (Masamitsu, Jul. 2006).*

(Continued)

*Primary Examiner* — David Cormier
*Assistant Examiner* — Irina Graf
(74) *Attorney, Agent, or Firm* — Mattingly & Malur, PC

(57) ABSTRACT

A function for checking whether components of an automatic analyzer properly operate is made available. A pressure sensor is installed in a sample path. A pressure waveform obtained during a washing water discharge operation 10 is used to check the opening/closing of a solenoid valve and the other operations of a dispensing mechanism. This function can also be exercised when a pressure sensor for a conventional sample suction check process is used. Even when the solenoid valve fails to open or close, an alarm is issued to indicate such a failure. This makes it possible to prevent a sample from thinning, thereby providing enhanced data reliability.

8 Claims, 5 Drawing Sheets

(56) References Cited

FOREIGN PATENT DOCUMENTS

| | | |
|---|---|---|
| JP | 2000-338115 A | 12/2000 |
| JP | 2002-98707 A | 4/2002 |
| JP | 2004-125780 A | 4/2004 |
| JP | 2005-17125 A | 1/2005 |
| JP | 2006-189259 A | 7/2006 |
| JP | 2008-58163 A | 3/2008 |

OTHER PUBLICATIONS

English Abstract of JP 2000046846 A (Hikita et .al, Feb. 2000).*

* cited by examiner

FIG. 6
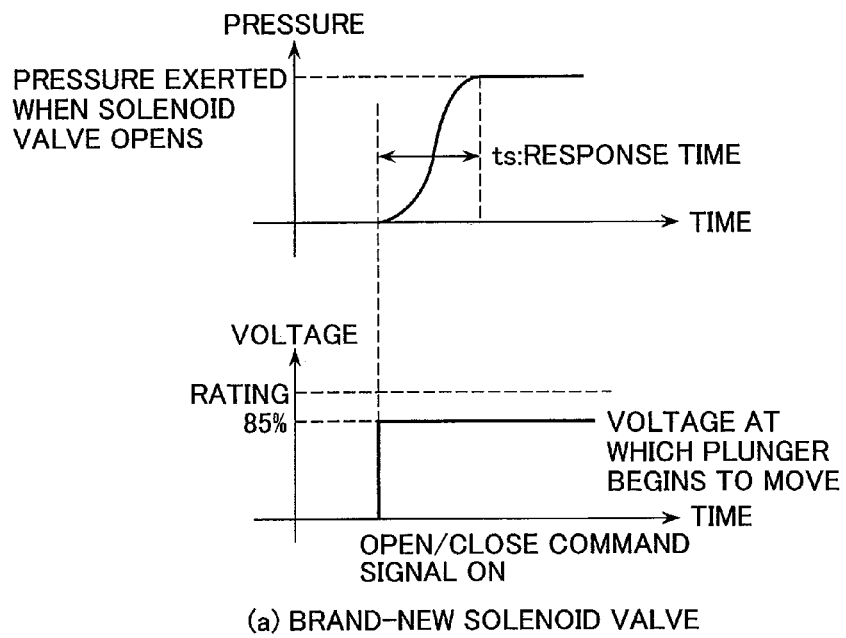
(a) BRAND-NEW SOLENOID VALVE
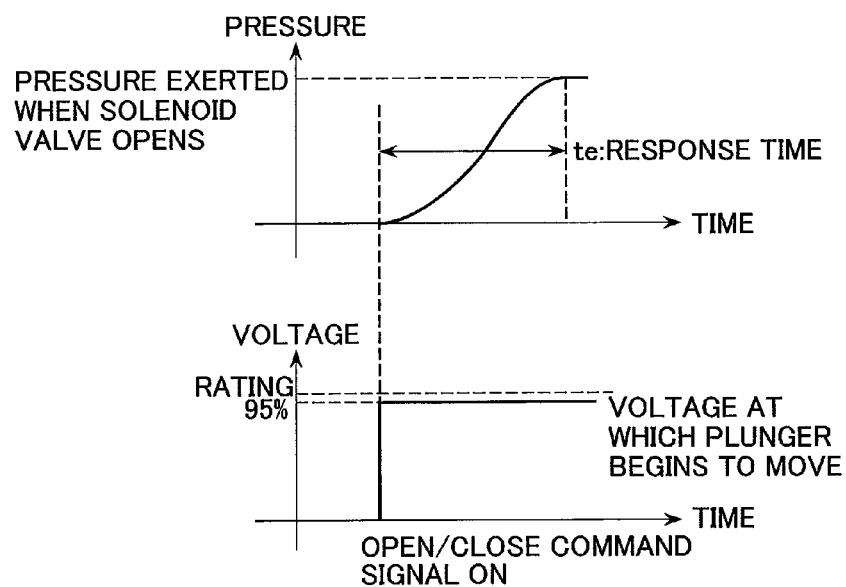
(b) SOLENOID VALVE USED 3 MILLION TIMES

AUTOMATIC ANALYZER INCLUDING PRESSURE SENSOR FOR WASHING SOLUTION

TECHNICAL FIELD

The present invention relates to an automatic analyzer that performs qualitative/quantitative analysis of a specific constituent in blood, urine, or other biological sample, and more particularly to an automatic analyzer that includes dispensing means for dispensing a predetermined amount of liquid.

BACKGROUND ART

When a clinical examination is conducted to analyze constituents of blood, urine, or other biological sample of a patient, the sample is caused to react with a reagent to perform qualitative/quantitative analysis of a target constituent. In this instance, a liquid supply mechanism called a dispensing mechanism is used to supply predetermined amounts of sample and reagent liquids to a reaction vessel in which the sample reacts with the reagent. The liquid supply mechanism causes a nozzle to suction a target liquid by producing a negative pressure within a nozzle with use of a syringe, diaphragm, or other pressure change means for the suctioning, and then discharges a predetermined amount of the liquid to the reaction vessel by producing a positive pressure within the nozzle by using the pressure change means.

The nozzle is washed after a sample and a reagent are suctioned and discharged because the nozzle will be used to dispense a different sample and a different reagent. External washing and internal washing are performed for nozzle washing purposes. In external washing, the nozzle is washed by pouring a washing solution onto the outer surface of the nozzle. In internal washing, the interior of the nozzle is washed by allowing the nozzle to discharge the washing solution. If the washing solution is used up before the completion of a nozzle washing process, the results of analysis are adversely affected due to insufficient washing. In view of such circumstances, a system described in Patent Document 1 detects the presence of the washing solution, and issues a warning when the washing solution is about to run short.

PRIOR ART REFERENCE

Patent Document

Patent Document 1: JP-2000-338115-A

SUMMARY OF THE INVENTION

Problem to be Solved by the Invention

Only the detection of whether or not there is a remaining washing solution is not sufficient to judge whether nozzle washing is normally completed. Even when an adequate amount of washing solution is available, the supply of washing solution may fall short of demand if the washing solution is supplied to the nozzle at improper timing (if the opening and closing of a piping valve for supplying the washing solution are improperly timed). When the nozzle is subjected to the aforementioned internal washing, washing water is supplied from a water supply unit. When a washing operation is performed, a solenoid valve positioned between the water supply unit and a sample dispensing syringe stays open for a predetermined period of time. As washing performance depends on the amount of water used for the washing operation, it is essential that the solenoid valve stay open for the predetermined period of time. If the solenoid valve is open for a period shorter than the predetermined period of time, insufficient washing may result. If, on the contrary, the solenoid valve is open for a period longer than the predetermined period of time, the washing water may be discharged at an irrelevant position.

An object of the present invention is to provide an automatic analyzer that is capable of checking whether a dispensing nozzle is being properly washed.

Means for Solving the Problem

In accomplishing the above object, according to one aspect of the present invention, there is provided an automatic analyzer including a dispensing nozzle, a dispensing syringe, a pressure sensor, a washing solution storage tank, a washing solution supply piping, and a judgment mechanism. The dispensing nozzle suctions and discharges a predetermined amount of liquid. The dispensing syringe changes the pressure in the dispensing nozzle. The pressure sensor is installed in a piping that connects the dispensing nozzle to the dispensing syringe. The washing solution storage tank stores a washing solution that washes the dispensing nozzle. The washing solution supply piping connects the washing solution storage tank to the dispensing syringe or the piping between the dispensing nozzle and the dispensing syringe. The judgment mechanism measures the output from the pressure sensor when the washing solution is supplied from the washing solution storage tank to the dispensing syringe or the piping between the dispensing nozzle and the dispensing syringe, and judges, in accordance with the measured output, whether washing is normally performed.

Preferably, the automatic analyzer includes a sample dispensing syringe, a sample dispensing unit, a water supply unit, a solenoid valve, a pressure sensor positioned between the sample dispensing syringe and the sample dispensing unit, means for analyzing and judging a signal output from the pressure sensor. The means for analyzing and judging a signal output from the pressure sensor analyzes and judges a signal generated when a sample is suctioned, a signal generated when the solenoid valve opens, and a signal generated when the solenoid valve closes.

Advantageous Effect of the Invention

The accuracy of analysis performed by an automatic analyzer can be maintained by preventing a nozzle washing failure.

BRIEF DESCRIPTION OF THE DRAWINGS

FIGS. 6(a) and 6(b) show the relationship between pressure and voltage that prevails before the solenoid valve opens.

MODE FOR CARRYING OUT THE INVENTION

Embodiments of the present invention will now be described with reference to the accompanying drawings.

First Embodiment

Figure 1:
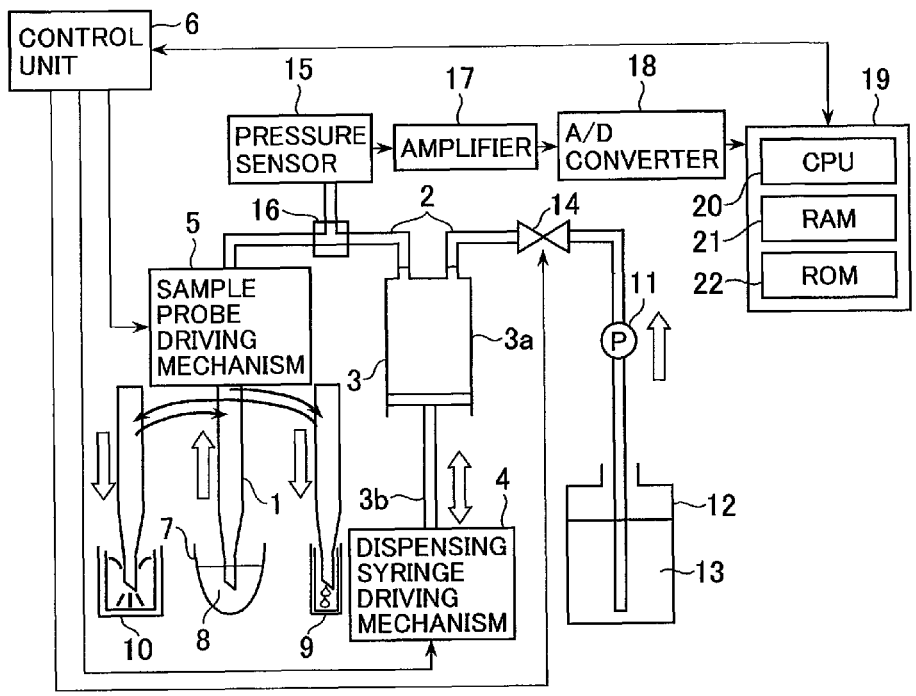
FIG. 1 is a diagram illustrating the configuration of an automatic analyzer according to the present invention.

FIG. 1 is a diagram illustrating the configuration of an automatic analyzer according to the present invention.

A sample probe 1 is connected to a dispensing syringe 3 through a tube 2. The interiors of these components are filled with a liquid. The dispensing syringe 3 includes a cylinder 3a and a plunger 3b. The plunger 3b is connected to a dispensing syringe driving mechanism 4. While the cylinder 3a is fixed, the dispensing syringe driving mechanism 4 drives the plunger 3b upward and downward to perform a sample dispensing operation. Further, as a sample probe driving mechanism 5 is connected to the sample probe 1, the sample probe 1 can be moved to a predetermined position. The dispensing syringe driving mechanism 4 and the sample probe driving mechanism 5 are controlled by a control unit 6.

When the sample probe driving mechanism 5 causes the sample probe 1 to descend and reach into the liquid of a sample 8 in a sample vessel 7, the dispensing syringe driving mechanism 4 causes the dispensing syringe 3 to perform a sample suction operation. Upon completion of the sample suction operation, the sample probe 1 moves to a sample discharge position 9 so that the dispensing syringe 3 performs a discharge operation. Upon completion of dispensing, the sample probe 1 moves to a washing position 10. A water supply pump 11 then causes washing water 13 in a water supply tank 12 to flow at high pressure and wash the sample probe 1. A relevant switching operation is performed by a solenoid valve 14 which is controlled by the control unit 6.

A pressure sensor 15 is connected through a branching block 16 to a dispensing flow passage system, which includes the sample probe 1, the tube 2, and the dispensing syringe 3.

A pressure signal from the pressure sensor 15 is amplified by an amplifier 17 and converted into a digital signal by an A/D converter 18. An output from the A/D converter 18 is forwarded to a microcomputer 19 in which a process described below is performed to judge whether dispensing is normally performed.

Figure 2:
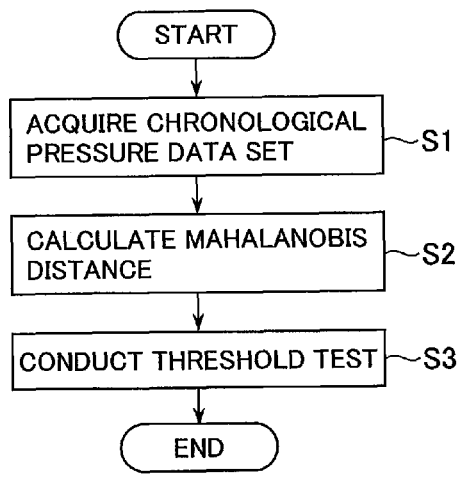
FIG. 2 is a flowchart illustrating an abnormality detection process that is performed by the automatic analyzer according to the present invention.

FIG. 2 is an exemplary flowchart illustrating an abnormality detection process that is performed by the automatic analyzer according to the present invention.

When the washing water is discharged or when the sample is suctioned, internal pressure changes, including minute ones, constantly occur. This causes the output from the pressure sensor to change accordingly. In step S1, the present invention acquires a changing pressure value successively in chronological order, and uses a set of the acquired pressure values (hereinafter referred to as a chronological pressure data set). Next, in step S2, the Mahalanobis distance is determined from the acquired chronological pressure data set. Although any analysis algorithm may be used, the use of the Mahalanobis distance is preferred because it provides the highest detection accuracy and is unlikely to be affected by a mechanical motion of the sample probe or the like. The Mahalanobis distance is used with a multivariate analysis method. The chronological pressure data set acquired when dispensing was normally completed is used as a reference (hereinafter referred to as the reference data). In step S3, the Mahalanobis distance is compared against the reference data to judge whether dispensing is normally performed.

Figure 3:
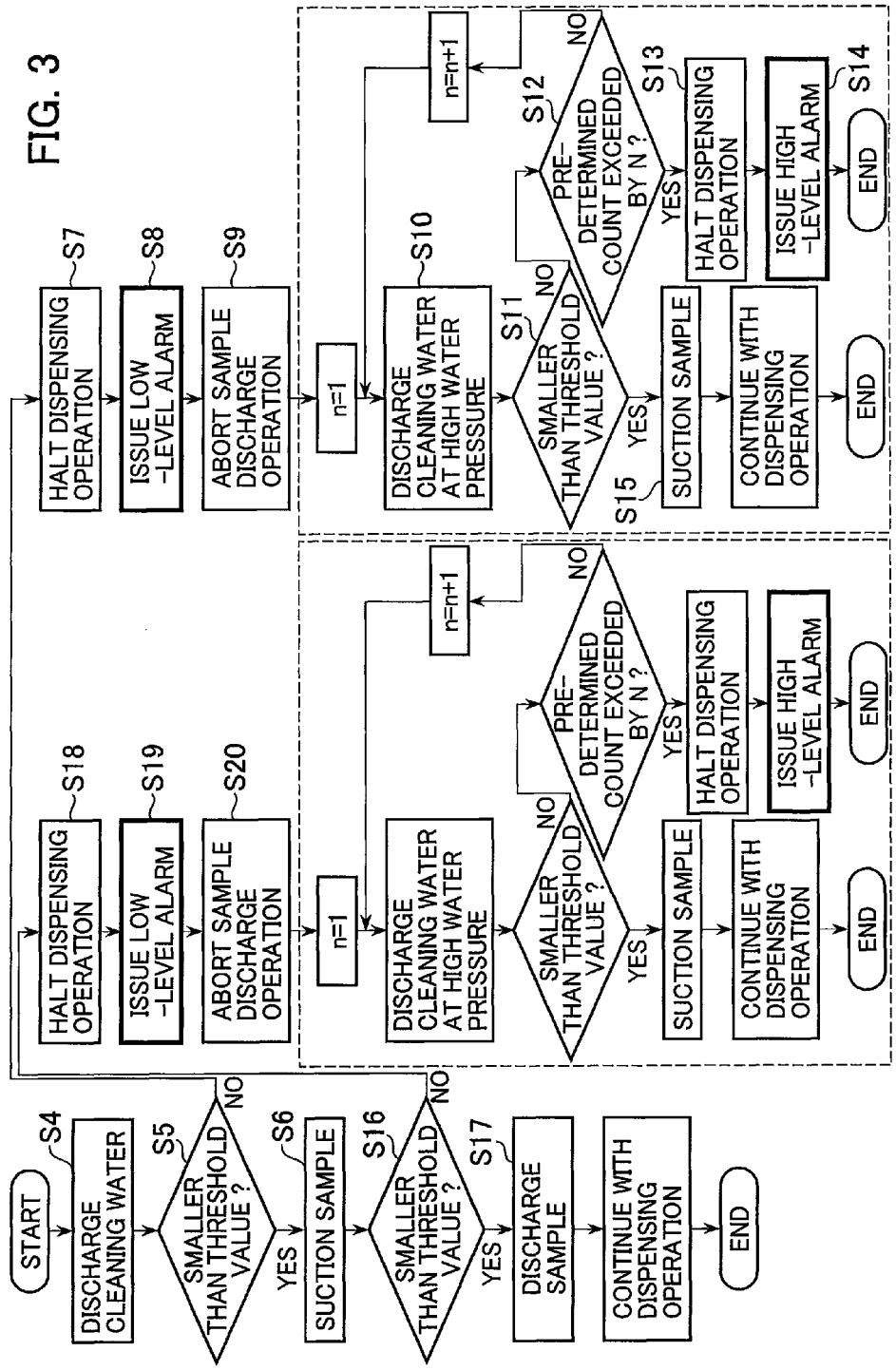
FIG. 3 is a flowchart illustrating how the automatic analyzer according to the present invention generates an alarm output when it finds an abnormality.

FIG. 3 is an exemplary flowchart illustrating how the automatic analyzer according to the present invention generates an alarm output when it finds an abnormality.

The washing water is discharged at a washing water discharge position (step S4), and the prevailing Mahalanobis distance is determined and compared against a threshold value (step S5).

When the result of comparison indicates that the washing water is normally discharged, the sample probe moves to a sample vessel position and performs a sample suction operation (step S6). When, on the other hand, the result of comparison does not indicate that the washing water is normally discharged, the sample probe comes to an immediate halt (step S7). Step S7 is performed to prevent the washing water from being added to the sample to decrease its concentration on the presumption that the detected abnormality is caused by an opening/closing failure of the solenoid valve. In step S8, the automatic analyzer not only halts the sample probe without moving it to a sample suction position, but also outputs an alarm (hereinafter referred to as a low-level alarm) to indicate that the last washing water discharge operation failed. In step S9, the automatic analyzer aborts the sample suction operation. In step S10, the automatic analyzer returns the sample probe to the washing water discharge position and discharges the washing water at high pressure to correct the opening/closing failure of the solenoid valve. It should be noted that the above operation may be performed by filling the probe with water, which is a function exercised in many automatic analyzers when, for instance, parts in a syringe are to be replaced. Subsequently, step S11 is performed to repeat a threshold test. Step S12 is then performed to discharge the washing water at high pressure until the threshold value is reached. When a predetermined high-pressure washing water discharge count is exceeded, step S13 is performed to stop a dispensing operation because it is conceivable that the abnormality may not be cleared by washing. The automatic analyzer then proceeds to step S14 and outputs an emergency stop alarm (hereinafter referred to as a high-level alarm) to indicate that a dispensing operation was not normally performed due to a washing water discharge failure. When the threshold test indicates normality after high-pressure washing water discharge, the automatic analyzer proceeds to step 15 and performs a sample suction operation.

After completion of the sample suction operation (step S6), step S16 is performed to determine the Mahalanobis distance provided by the sample suction operation and compare the Mahalanobis distance against a threshold value. The threshold value used in step S16 differs from that used for washing water discharge judgment. The automatic analyzer completes the above process before a sample discharge operation, and determines, in accordance with the result of judgment, whether the sample discharge operation should be performed.

When it is concluded that the sample is normally suctioned, the automatic analyzer moves the sample probe to the sample discharge position and discharges the sample (step S17). If any abnormality is found, the automatic analyzer halts the sample probe (step S18), outputs a low-level alarm (step S19), and aborts the sample discharge operation (step S20). Subsequently, the automatic analyzer proceeds to perform a washing water discharge operation at high pressure, as is the case where an abnormality is found during a washing water discharge operation.

Figure 4:
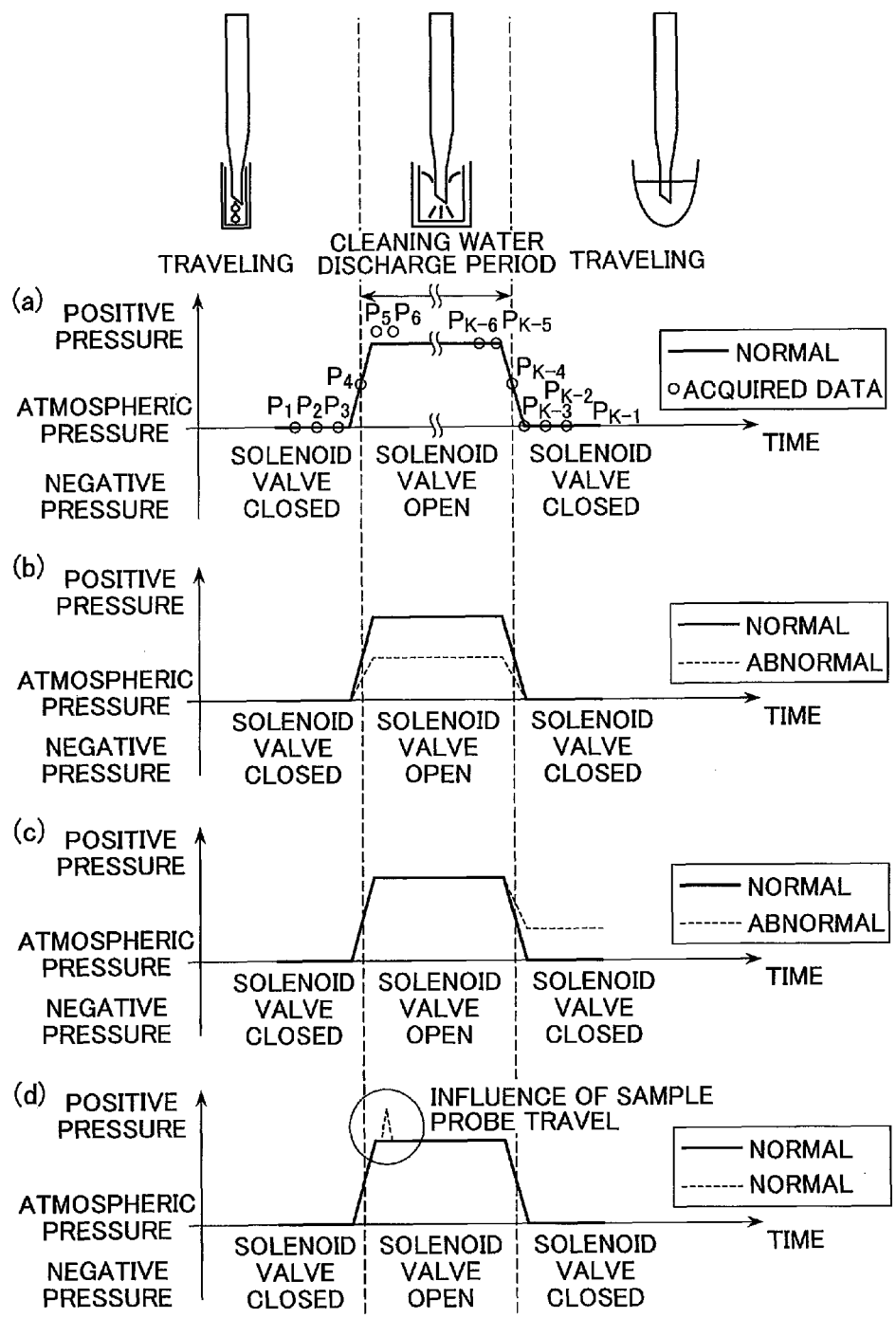
FIGS. 4(a) to 4(d) show pressure changes monitored when a solenoid valve is opened and closed.

FIGS. 4(a) to 4(d) show exemplary pressure changes that are monitored with main reference to a washing water discharge period according to the present invention when the solenoid valve is opened and closed. From a changing pressure variation waveform, pressure values prevailing at k points are acquired as shown in FIG. 4(a).

Reference data acquisition points are centered with respect to the washing water discharge period. Although detection can be accomplished by using a set of chronological pressure data obtained during the washing water discharge period only, several pressure values obtained before and after such a period are also included to provide enhanced accuracy. The accuracy may be further enhanced by acquiring pressure variations encountered during a sample suction period and a sample discharge period.

Data to be included in the chronological pressure data set may be acquired at fixed intervals or at variable intervals. The data may be acquired at relatively short intervals during a dispensing period during which abnormality is likely to occur. On the contrary, during a period during which abnormality is unlikely to occur, the data may be acquired at relatively long intervals. In any case, the data need not be acquired at equal intervals. However, there is no telling where in the washing water discharge period a discharge abnormality occurs. It is therefore preferred that the data be acquired at equal intervals during the washing water discharge period. Acquiring the data at excessively long intervals may result in the failure to detect abnormality. On the contrary, acquiring the data at excessively short intervals may increase the time required for arithmetic processing. Therefore, the data acquisition intervals should be increased without causing an abnormality detection failure.

The k-point data to be included in the chronological pressure data set may be acquired either by specifying the points of time at which the k-point data are to be acquired and then acquiring only the k-point data or by acquiring data at the minimum permissible intervals and then thinning the acquired data to obtain k-point data.

When the above procedure is performed in relation to a normal discharge operation, the reference chronological pressure data set can be obtained. The normal discharge operation is accomplished when normal purified water is discharged in a state where a normal discharge operation can be properly performed. The normal purified water is obtained when mainly salt and residual chlorine are thoroughly removed from water. The state where a normal discharge operation can be properly performed is a state where variations in the components of a sample dispensing mechanism, such as sample probe inside diameter variation and pressure sensor sensitivity variation, are held within a predetermined tolerance range without regard to various factors, such as individual variability in manufacture, the influence of external environment, and deterioration, and the sample dispensing mechanism is normal, for instance, without causing the sample probe to be clogged and can deliver its full-expected performance.

The reference data is not a mere collection of statistical data but a set of statistical data obtained while no abnormality exists as described above. Therefore, the reference data should be created in such a manner that it includes no abnormal data. However, if there are variations falling within a normal range such as sample probe inside diameter variation and pressure sensor sensitivity variation, it is preferred that the reference data be obtained while such variations are allowed to occur positively. The reason is that the accuracy of abnormality detection will increase when the reference data is obtained in the manner described above.

A large number of events n should be involved in the reference data because it will increase the accuracy of abnormality detection. However, the number of events n is excessive, the economical cost will unduly increase. It is therefore essential that the number of events n be determined while considering the economical cost and the accuracy of detection.

The chronological pressure data set and reference data obtained as described above should be used only when the associated dispensing amount is applied to dispensing. The reason is that a dispensing speed appropriate for the employed dispensing amount and dispensing syringe and sample probe driving sequences that are appropriate for the employed dispensing amount are used, and that the pressure variation waveform changes in accordance with the dispensing speed and the dispensing syringe and sample probe driving sequences. In other words, it is preferred that the number of data to be included in the chronological pressure data set and the method of chronological pressure data set acquisition be changed as appropriate for each dispending amount, and that the reference data be prepared for each dispensing amount.

The flow for conducting the threshold test by using the chronological pressure data set and reference data which are obtained in the manner described above is as described in Patent Document 1. According to the Mahalanobis distance, the broken lines in FIGS. 4(b) and 4(c) can be judged to be abnormal, and the broken line in FIG. 4(d) which shows disturbance caused, for instance, by sample probe movement can be judged to be normal.

Second Embodiment

Recently developed automatic analyzers tend to dispense small amounts. It is therefore demanded that the amounts of sample and reagent dispensed from a sample probe and a reagent probe be accurate and reproducible.

However, the accuracy of dispensing becomes unstable due to machining tolerance, for instance, on probe inside diameter or on a syringe plunger. In addition, the automatic analyzers tend to become smaller in size, and relatively soft tubes, for example, made of silicon are routed within the automatic analyzers. Naturally, a soft tube is used to connect a sample syringe to a sample probe. Therefore, the accuracy of dispensing becomes unstable due to thermal expansion of the tube. In other words, it is demanded that machining error and environmentally-induced unavoidable dispensing error be compensated for. This demand can be satisfied by installing the pressure sensor according to the present invention. When the pressure sensor according to the present invention is installed, operational corrections can be made in accordance with the absolute value of a positive pressure that is detected by the pressure sensor during a washing water discharge operation. When, for instance, the absolute value is greater than the reference data, it means that the actual dispensing amount is larger than a setting. Therefore, when an operational correction is made to compensate for the difference between the actual dispensing amount and the setting, an appropriate amount of sample can be discharged in accordance with the setting.

Third Embodiment

It is generally understood that solenoid valves reach the end of their useful life when they are operated approximately three million times. In biochemical automatic analyzers, however, it is anticipated that the solenoid valves may be used a larger number of times than the above. It should also be noted that the solenoid valves may reach the end of their useful life earlier than predicted depending, for instance, on their individual variability, the employed liquid, and the surrounding environment.

Figure 5:
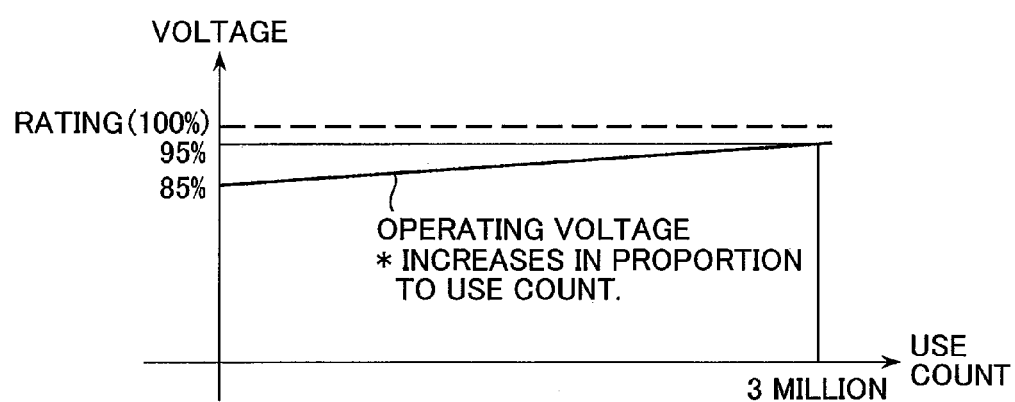
FIG. 5 is a diagram illustrating the correlation between the use count and operating voltage of the solenoid valve.

FIG. 5 is a diagram illustrating a phenomenon that occurs when a solenoid valve is used an increased number of times. The operating voltage indicated in FIG. 5 is a voltage at which an iron core in a solenoid (this iron core will be hereinafter referred to as the plunger) begins to move after an open/close command signal for the solenoid valve is turned ON. When it is assumed that the rated operating voltage is 100%, the operating voltage for an unused solenoid valve is approximately 85%. However, when the solenoid valve is operated three million times and reaches the end of the useful life thereof, the operating voltage therefor is approximately 95%.

The above-mentioned operating voltage correlates with the response time of the solenoid valve. More specifically, the higher the operating voltage, the longer the response time as indicated in FIGS. 6(*a*) and 6(*b*). This phenomenon can be used to judge whether the solenoid valve has reached the end of the useful life thereof.

The Mahalanobis distance is compared against a chronological pressure data set obtained when a new solenoid valve is normally operated, and the result of comparison is used to judge whether the solenoid valve has reached the end of the useful life thereof. As regards the Mahalanobis distance, the data to be included in the chronological pressure data set is acquired at variable intervals. In this instance, therefore, the useful life of the solenoid valve can be determined with increased accuracy by decreasing the interval between the instant at which the pressure begins to rise during a washing water discharge operation and the instant at which the pressure is completely stabilized. If a magnetic field remains in the solenoid or plunger, the operating voltage lowers so that the useful life cannot be determined accurately. Therefore, when the solenoid valve is to be operated to exercise the above-described function, it is preferred that the solenoid valve be operated for starting the automatic analyzer or for performing a maintenance task because the elapsed time since the last operation is long enough. Further, as the response time of the solenoid valve is affected by temperature, it is necessary to pay attention to the environment when exercising the above-described function.

As described above, the reference data for the third embodiment differs from the reference data for the first embodiment in the purpose of use, in the timing of use, and in the employed environment. It is therefore preferred that the reference data for the third embodiment be set up as the data separate from the reference data for the first embodiment.

DESCRIPTION OF REFERENCE NUMERALS

1 . . . Sample probe
2 . . . Tube
3 . . . Dispensing syringe
4 . . . Dispensing syringe driving mechanism
5 . . . Sample probe driving mechanism
6 . . . Control unit
7 . . . Sample vessel
8 . . . Sample
9 . . . Sample discharge position
10 . . . Washing position
11 . . . Water supply pump
12 . . . Water supply tank
13 . . . Washing water
14 . . . Solenoid valve
15 . . . Pressure sensor
16 . . . Branching block
17 . . . Amplifier
18 . . . A/D converter
19 . . . Microcomputer

The invention claimed is:

1. An automatic analyzer including:
a dispensing nozzle that suctions and discharges a predetermined amount of liquid;
a dispensing syringe that is connected the dispensing nozzle;
a washing solution storage tank that stores a washing solution for washing the dispensing nozzle; and
a washing solution supply piping that connects the washing solution storage tank to the dispensing syringe and connects the dispensing nozzle to the dispensing syringe;
a pump that is installed in the washing solution supply piping that connects the washing solution storage tank to the dispensing syringe that supplies the washing water under pressure;
a pressure sensor that is installed in the washing solution supply piping that connects the dispensing nozzle to the dispensing syringe;
a solenoid valve that is installed in the washing solution supply piping; and
a processor that receives an output from the pressure sensor when the washing solution is supplied from the washing solution storage tank to the dispensing syringe or when the washing solution is supplied to the dispensing nozzle from the dispensing syringe, and the processor is programmed to determine that an opening and closing of the solenoid valve is not properly timed and washing is not normally performed when a time interval from when the pressure starts to change when the solenoid valve opens or closes until the pressure stabilizes is greater than or equal to a predetermined value.

2. The automatic analyzer according to claim 1, wherein the solenoid valve is installed in the washing solution supply piping that connects the washing solution storage tank to the dispensing syringe.

3. The automatic analyzer according to claim 2, wherein, when the processor concludes that the opening and closing of the solenoid valve is not properly timed and washing is not normally performed, the processor issues a warning indicative of abnormal washing.

4. The automatic analyzer according to claim 1, wherein the processor chronologically measures the output from the pressure sensor before and after an issuance of the open/close command signal for the solenoid valve, and judges, in accordance with chronological pressure changes, whether washing is normally performed.

5. The automatic analyzer according to claim 4, wherein, when the processor concludes that the opening and closing of the solenoid valve is not properly timed and washing is not normally performed, the processor issues a warning indicative of abnormal washing.

6. The automatic analyzer according to claim 1, wherein the processor uses a Mahalanobis distance to judge whether washing is normally performed.

7. The automatic analyzer according to claim 6, wherein, when the processor concludes that the opening and closing of the solenoid valve is not properly timed and washing is not normally performed, the processor issues a warning indicative of abnormal washing.

8. The automatic analyzer according to claim 1, wherein, when the processor concludes that the opening and closing of the solenoid valve is not properly timed and washing is not normally performed, the processor issues a warning indicative of abnormal washing.

* * * * *